United States Patent [19]

Grundei

[11] Patent Number: 4,714,471
[45] Date of Patent: Dec. 22, 1987

[54] FEMUR PROSTHESIS PART OF A KNEE JOINT ENDOPROSTHESIS

[75] Inventor: Hans Grundei, Lübeck, Fed. Rep. of Germany

[73] Assignee: S + G Implants GmbH, Lübeck, Fed. Rep. of Germany

[21] Appl. No.: 921,840

[22] Filed: Oct. 22, 1986

Related U.S. Application Data

[63] Continuation of Ser. No. 779,512, Sep. 24, 1985, abandoned.

[30] Foreign Application Priority Data

Sep. 26, 1984 [DE] Fed. Rep. of Germany ....... 3435243

[51] Int. Cl.[4] .............................................. A61F 2/38
[52] U.S. Cl. ........................................ 623/20; 623/18
[58] Field of Search .............................. 623/20, 33, 18

[56] References Cited

U.S. PATENT DOCUMENTS

| | | | |
|---|---|---|---|
| 4,262,368 | 4/1981 | Lacey | 623/20 |
| 4,301,553 | 11/1981 | Noiles | 623/20 |
| 4,462,120 | 8/1984 | Rambert et al. | 123/20 |

Primary Examiner—Richard J. Apley
Assistant Examiner—Alan W. Cannon
Attorney, Agent, or Firm—Balogh, Osann, Kramer, Dvorak, Genova & Traub

[57] ABSTRACT

The femur prosthesis part consists of a stem to be anchored in the femur bone and the sledge part, separate from and to be connected to the stem. The stem extends laterally like a fork over the connecting bridge of the sledges of the sledge part, and the ends of the fork arms have flanges which form stops against the lower end of the femur bone and, after connection of the sledge part to the stem, are supported on the top of the sledges.

1 Claim, 4 Drawing Figures

FEMUR PROSTHESIS PART OF A KNEE JOINT ENDOPROSTHESIS

This application is a continuation of application Ser. No. 779,512, filed Sept. 24, 1985, now abandoned.

BACKGROUND OF THE INVENTION

1. Field of the Invention

The invention relates to the femur prosthesis part of a knee joint endoprosthesis, supported by sledges on tibia slide surfaces, and the front connecting bridge of its sledges being provided with an upward-tapering conical pin for engagement by static friction in a matching bore of a stem to be anchored in the femur bone.

2. Description of the Prior Art

It is known from German patent specification No. 2 549 819 to shape femur prosthesis parts of knee joint endoprostheses in such way that the stem to be introduced into the femur bone is provided on the outer periphery with, for example, annular ribs which have a saw tooth-like profile in the longitudinal direction. As a result, the stem can be anchored more readily and irreleasably as a unit in the femoral bone and it can be connected to the sledge part, supported on slide surfaces of the tibia plateaus, by means of an upper conical pin which is insertable with static friction into a corresponding bore in the stem, in order thus to enable the tibia part to be exchanged.

Hitherto, the stem was anchored in the femur bone in such a way that it could become loose after a prolonged period and, above all, it was possible for the stem, when inserted or knocked into the medullary cavity of the femur bone, to penetrate either too deeply or not sufficiently deeply into the medullary cavity, so that a perfect fit of the prosthesis was not achievable in this way under some circumstances.

OBJECTS AND SUMMARY OF THE INVENTION

It is the object of the invention to enable the stem of the femur prosthesis part of a knee joint endoprosthesis to be fixed with certainty at its depth of penetration into the medullary cavity of the femur bone.

In the femur prosthesis part mentioned at the outset, the object is achieved when the stem, which advantageously is to be anchored irreleasably in the femur bone, extends laterally like a fork over the connecting bridge of the sledges, and when the ends of the fork arms have flanges which form stops against the lower end of the femur bone and, after a fitting engagement of the conical pin in the stem bore, are supported on the top of the sledges.

Owing to this solution, the flanges on the fork ends of the stem to be driven into the medullary cavity bear against the prepared plane and face of the femur bone, so that the depth of penetration of the stem and hence the position of the sledge part to be connected to the stem are fixed with certainty.

BRIEF DESCRIPTION OF THE DRAWINGS

The invention will now be explained, by way of example, with reference to the accompanying partly diagrammatic drawings, in which.

DETAILED DESCRIPTION OF THE PREFERRED EMBODIMENT

Figure 3:
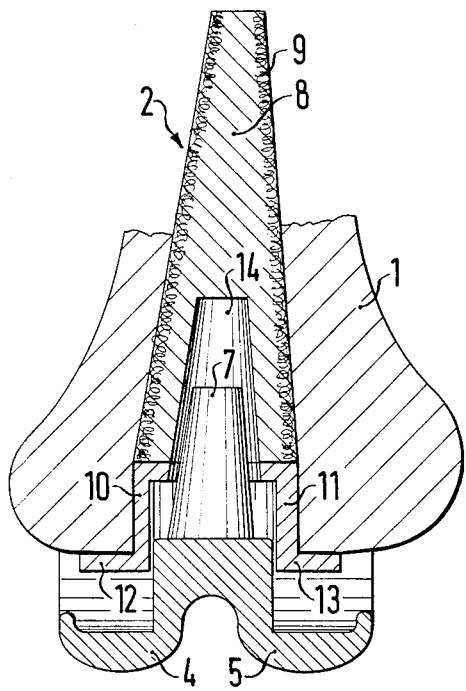
FIG. 3 is a section along line III to III of FIG. 1, with partial engagement of the part according to FIG. 1 in a stem to be anchored in the femur bone.
Figure 1:
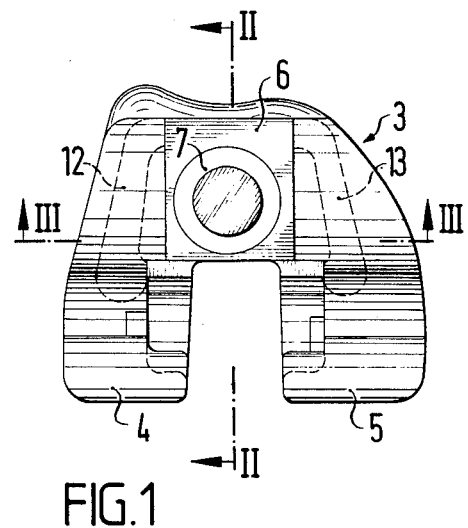
FIG. 1 is a plan view of a part, exhibiting the sledges, of a femur prosthesis part of a knee joint endoprosthesis.
Figure 4:
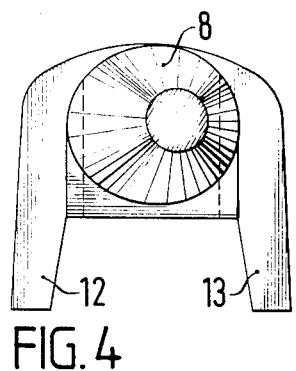
FIG. 4 is a plan view of the stem to be anchored in the femur bone.
Figure 2:
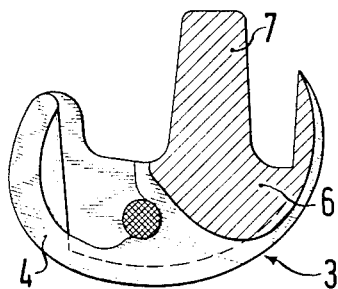
FIG. 2 is a section along line II to II of FIG. 1.

The femur prosthesis part of a knee joint endoprosthesis is composed of a stem 2 to be anchored in the femur bone 1 and the sledge part 3 to be connected to the stem. The sledge part 3 consists in known manner of two sledges 4 and 5 which are to be supported on the slide surfaces of a known tibia prosthesis part (not shown) and are connected to one another by a bridge 6. The bridge 6 is provided with a fixing pin 7 tapering conically upwards.

The metal stem 8 to be anchored in the medullary cavity of the bone 1 is advantageously provided with an open-cell outer metal layer 9, the cells of which permit bone tissue to grow in, with subsequent formation of bone. However, the stem can also have a smooth surface and is then cemented in position. The stem 8 has such a shape that its lower end extends laterally with spaced apart fork arms 10,11 over the bridge 6 of the sledge part 3. The ends of the fork arms 10,11 are provided with lateral flanges 12 and 13 which, when the stem 8 is driven in, bear as stops against the lower cut face of the femur bone 1 and hence limit and fix the depths of penetration of the stem into the medullary cavity of the bone. The sledge part 3 can then be connected to the stem 8 by introducing the conical pin 7 with static friction into a tapering cone-shaped bore 14 of the stem 8 which bore forms a U-profile, the flanges 12 and 13 being supported on the upward-pointing faces of the sledges 4 and 5. As a result, the connection of the femur prosthesis parts to the femur bone is made in such a way that it allows the sledge part to be released from the anchored stem, if this becomes necessary.

Whilst the invention and many of its attendant advantages will be understood from the foregoing description, it will be apparent that various changes may be made in the form, construction and arrangement of the parts without departing from the spirit and scope of the invention or sacrificing all of its material advantages, the form hereinbefore described merely, being a preferred embodiment thereof.

What is claimed is:

1. A femur prosthesis part of a knee joint endoprosthesis comprising a pair of convex sledges connected by a bridge and adapted to be supported on concave tibia slide surfaces, comprising a metallic stem of the femur prosthesis part to be anchored irreleasably by an open-cell metallic layer in the hole of the femur bone, said stem being provided at its lower end with a tapering cone-shaped bore and downwardly extending fork arms provided with lateral flanges having upper surfaces for supporting the lower cut face of the femur bone, said fork arms defining therebetween a bore having tapered walls communicating with said tapered cone-shaped bore, a conical pin having a tapered wall surface for engagement with tapered walls of said bores, said conical pin being supported by said bridge for insertion into said bores, said pair of sledges having depressions to accomodate and receive the undersurfaces of said lateral flanges.

* * * * *